(12) United States Patent
Carls et al.

(10) Patent No.: US 8,333,791 B2
(45) Date of Patent: Dec. 18, 2012

(54) MEDICAL IMPLANT WITH TIE CONFIGURED TO DELIVER A THERAPEUTIC SUBSTANCE

(75) Inventors: Thomas A. Carls, Memphis, TN (US); Newton H. Metcalf, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 309 days.

(21) Appl. No.: 12/429,290

(22) Filed: Apr. 24, 2009

(65) Prior Publication Data
US 2010/0274289 A1 Oct. 28, 2010

(51) Int. Cl.
*A61B 17/70* (2006.01)

(52) U.S. Cl. ...... 606/263; 606/246; 606/279; 623/17.11

(58) Field of Classification Search ............ 606/74, 606/246–299; 623/17.11–17.16
See application file for complete search history.

(56) References Cited

U.S. PATENT DOCUMENTS

| | | | |
|---|---|---|---|
| 4,009,509 A | 3/1977 | McCormick | |
| 4,922,926 A | 5/1990 | Hirschberg | |
| 5,154,182 A | 10/1992 | Moaddeb | |
| 5,868,711 A | 2/1999 | Kramer et al. | |
| 5,972,366 A | 10/1999 | Haynes et al. | |
| 6,361,780 B1 | 3/2002 | Ley et al. | |
| 6,416,548 B2 | 7/2002 | Chinn et al. | |
| 7,108,701 B2 * | 9/2006 | Evens et al. | 606/153 |
| 2002/0004683 A1 * | 1/2002 | Michelson | 623/17.16 |
| 2002/0138077 A1 * | 9/2002 | Ferree | 606/61 |
| 2002/0156489 A1 | 10/2002 | Gellman et al. | |
| 2002/0177863 A1 | 11/2002 | Mandel et al. | |
| 2004/0030338 A1 * | 2/2004 | Paul | 606/69 |
| 2004/0073221 A1 | 4/2004 | Biscup | |
| 2004/0142013 A1 | 7/2004 | Rubsamen | |
| 2004/0193166 A1 | 9/2004 | Biscup | |
| 2004/0243130 A1 | 12/2004 | Biscup | |
| 2005/0216010 A1 | 9/2005 | Michelson | |
| 2005/0267543 A1 | 12/2005 | Heruth et al. | |
| 2006/0036253 A1 | 2/2006 | Leroux | |
| 2006/0039947 A1 | 2/2006 | Schmidmaier et al. | |
| 2006/0247623 A1 * | 11/2006 | Anderson et al. | 606/61 |
| 2007/0190104 A1 | 8/2007 | Kamath et al. | |
| 2007/0224243 A1 | 9/2007 | Bayston | |
| 2007/0248640 A1 | 10/2007 | Karabey et al. | |
| 2007/0254008 A1 | 11/2007 | Rubsamen | |
| 2007/0254009 A1 | 11/2007 | Rubsamen | |
| 2009/0010989 A1 | 1/2009 | Peters | |
| 2009/0017090 A1 | 1/2009 | Arensdorf et al. | |
| 2009/0024165 A1 * | 1/2009 | Ferree | 606/246 |
| 2009/0053278 A1 | 2/2009 | Fatora et al. | |

* cited by examiner

*Primary Examiner* — Alvin Stewart
*Assistant Examiner* — Nicholas Plionis

(57) ABSTRACT

Embodiments of the invention comprise a medical implant that delivers a therapeutic substance. In some embodiments, a component that carries a therapeutic substance is a tie secured to all or a portion of a surgical construct, surgical screw, pedicle screw, spinal rod cross-link, other element or device, or an anatomical structure.

20 Claims, 5 Drawing Sheets

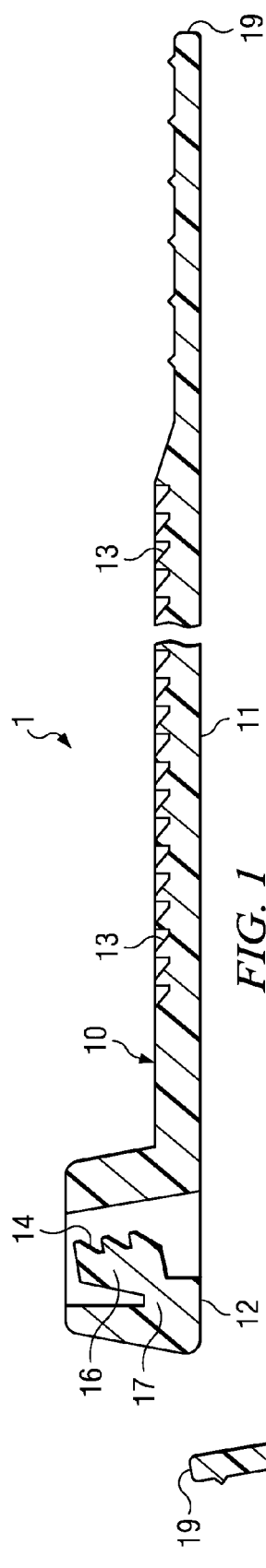
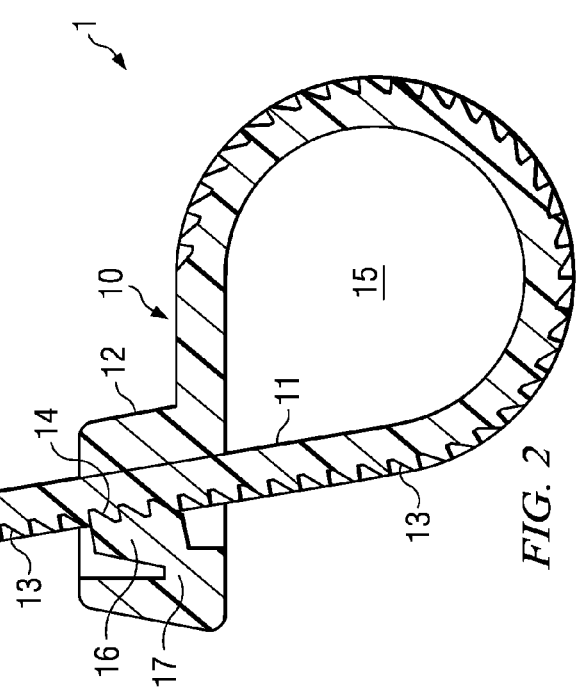

US 8,333,791 B2

MEDICAL IMPLANT WITH TIE CONFIGURED TO DELIVER A THERAPEUTIC SUBSTANCE

FIELD OF THE INVENTION

The present invention relates generally to the field of medical implants, and more particularly relates to a medical implant that is configured to deliver a therapeutic substance and methods of applying a therapeutic substance.

BACKGROUND

The use of therapeutic substances in combination with medical implants is a growing trend and has beneficial characteristics in many treatments. Therapeutic substances may be useful in promoting healing, fighting infection and disease by killing various pathogens such as bacteria, viruses, and microorganisms, promoting favorable cellular activity, killing cancer cells, or any of a wide variety of beneficial results. It may be advantageous to associate a therapeutic substance with a medical implant where the medical implant is implanted in a particularly advantageous location for effective application of the therapeutic substance.

It is a continuing challenge in the art to provide medical implants that may be conveniently and securely placed to deliver effective amounts of therapeutic substances in effective locations. Improved devices may provide secure connection to anatomical structures or to other medical device structures. It may be favorable for some improved implants that are capable of delivering a therapeutic substance to capture and securely fasten to existing medical device structures so that limited or no alteration to existing medical devices is necessary to implement the improved medical implants. It may be advantageous to provide medical implants capable of delivering a therapeutic substance that may be placed in a sequence that is complementary to existing surgical procedures.

SUMMARY

An embodiment of the invention is a medical implant configured to deliver a therapeutic substance. The medical implant may include a tie configured to couple with one or more of a medical device and an anatomical structure. The tie may particularly include a strap, and a pawl configured to receive the strap to form a loop comprising at least a portion of the strap and at least a portion of the pawl. The medical implant may also include a therapeutic substance incorporated with the tie. In some embodiments, the strap is retained in the pawl and prevented from moving out of the pawl as the strap is advanced into the pawl to lock the size of the loop at a progressively smaller size as the strap is advanced into the pawl. The tie may also be configured to release at least a portion of the therapeutic substance when the tie is exposed to an at least in part aqueous substance.

Another embodiment of the invention is a method of applying a therapeutic substance. The method may include receiving a tie that incorporates a therapeutic substance. The tie may include at least a strap, and a pawl configured to receive the strap to form a loop comprising at least a portion of the strap and at least a portion of the pawl. The method may also include wrapping the strap around at least a portion of a medical device and tightening the loop by moving the strap relative to the pawl to connect the tie to the medical device.

Yet another embodiment of the invention is a method of applying a therapeutic substance to a patient. The method may include receiving a tie that incorporates a therapeutic substance, where the tie includes at least a strap, and a pawl configured to receive the strap to form a loop comprising at least a portion of the strap and at least a portion of the pawl. The method may also include wrapping the strap around at least a portion of an anatomical structure of the patient, and tightening the loop by moving the strap relative to the pawl to connect the tie to the patient.

BRIEF DESCRIPTION OF THE DRAWINGS

FIG. 1 is a cross-sectional elevation view of an embodiment of a medical implant that contains a therapeutic substance.

FIG. 2 is a cross-sectional elevation view of the embodiment of FIG. 1 forming a loop with portions of the medical implant.

DETAILED DESCRIPTION

Figure 3:
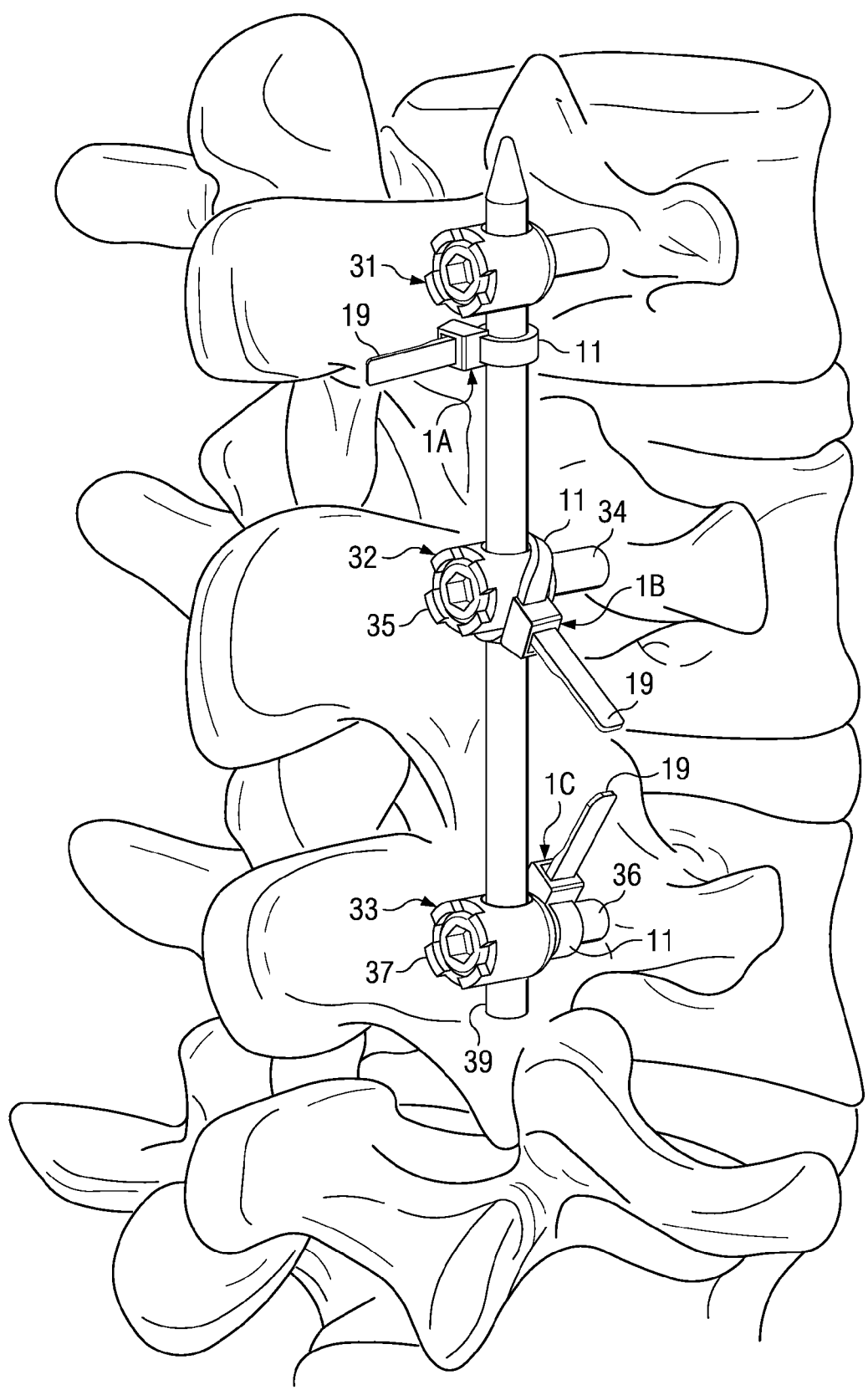
FIG. 3 is a perspective view of embodiments of a medical implant coupled to spinal screws and a spinal rod in various configurations.

A medical implant 1 configured to deliver a therapeutic substance is illustrated in FIGS. 1 and 2. The medical implant 1 is shown in cross-sectional views. The medical implant 1 includes a tie 10 and a therapeutic substance that is incorporated with the tie 10. The tie 10 is configured to couple with one or more of a medical device and an anatomical structure. The illustrated tie 10 includes a strap 11 and a pawl 12. The therapeutic substance may be incorporated in all or a part of the strap 11 and the pawl 12. The strap 11 includes teeth 13 on one side of the strap 11. The teeth 13 that are shown in FIGS. 1 and 2 are ratchet teeth that are designed to allow movement in a first direction, but to stop movement in a second direction substantially opposite from the first direction. In other embodiments, teeth on one or more sides of the strap 13 may be, without limitation, gear teeth that are part of a rack and pinion drive system or ridges or other roughenings that provide one or more places to grasp, catch, or engage. In some embodiments, a strap may friction fit with or be securely grasped by a pawl and not include any teeth or similar mechanisms.

The strap 11 is shown entering the pawl 12 in FIG. 2 approximately perpendicular to the direction from which the strap 11 extends from the pawl 12 at the strap's permanent connection end. However, in various embodiments the strap 11 may enter into or couple with the pawl 12 at any functional angle or from any functional orientation. For example and without limitation, the strap 11 may loop completely around so that the distal end 19 substantially aligns with the direction from which the strap 11 extends from a pawl.

In the illustrated embodiment, the pawl 12 is configured to receive the strap 11 to form a loop 15. The loop 15 of some embodiments includes at least a portion of the strap 11 and at least a portion of the pawl 12. The illustrated pawl 12 includes stay teeth 14 configured to engage with the teeth 13 on the strap 11. The stay teeth 14 are part of a shoe 16 connected to the remainder of the pawl 12 through a living hinge 17. In operation of the illustrated embodiment, the strap 11 is retained in the pawl 12 and prevented from moving out of the pawl 12 as the strap 11 is advanced into the pawl 12. As used herein, moving or advancement "into" the pawl 12 is movement that includes the distal end 19 of the strap 11 first contacting the pawl 12, or once in contact with the pawl 12, continuing to move further away from the pawl 12. Moving "out of" the pawl 12 includes moving the strap 11 such that the distal end 19 is moving toward and then through and out of the pawl 12. The illustrated tie 10 is configured to lock the size of the loop 15 at progressively smaller sizes as the strap 11 is advanced into the pawl 12. The teeth 13 of the strap 11 interface with the stay teeth 14 of the shoe 16 to progressively lock the tie 10 as the strap 11 is advanced into the pawl 12. The shoe 16 is biased toward the strap 11, as illustrated in FIG. 2. The shoe 16 articulates with respect to the rest of the pawl 12 about the living hinge 17, but because of its bias, the stay teeth 14 are forced into engagement with the teeth 13 of the strap 11. In other embodiments, the engagement between a pawl and a strap may be of any effective type. For example and without limitation, the engagement may be frictional, may be driven or held in place by a rack and pinion mechanism, may include gears or teeth on multiple sides of a strap, or may be driven or controlled by instruments or inputs external to a tie. A tie of various embodiments may include a release mechanism for loosening, moving, or ex-planting the tie. The tie 10 of the embodiment shown in FIGS. 1 and 2 may be released by inserting a tool between the teeth 13 and the stay teeth 14. Use of a tool in this manner may hinge the shoe 16 away from the strap 11 and allow the strap 11 to move out of the pawl 12. Other embodiments may include release mechanisms with different mechanism but that achieve the same effect of allowing a loop, such as the loop 15, to be opened and a strap to be moved out of a pawl.

The medical implant 1 will be described herein with specific reference to embodiments that may comprise minor variations to the medical implant 1. Each of the medical implants 1A, 1B, 1C, 1D, 1E, 1F, 1G, 1H, 1J, 1K, 1L, 1M, and 1N is essentially similar to the medical implant 1 and will be referred to as having like numbered components that may be more specifically described with reference to FIGS. 1 and 2.

In the illustrated embodiment, a therapeutic substance is incorporated with the tie 10 to form the medical implant 1. The tie 10 may be configured to release at least a portion of the therapeutic substance when the tie 10 is exposed to an at least in part aqueous substance. The aqueous substances of some embodiments are bodily fluids. The bodily fluids may contact all or a part of the medical implant 1 when the medical implant 1 is enclosed at least in part within a patient.

Embodiments of the tie 10 in whole or in part may be constructed of biocompatible materials of various types. Examples of tie materials include, but are not limited to, non-reinforced polymers, reinforced polymer composites, metals, ceramics and combinations thereof. In some embodiments, the tie 10 may be constructed of sections of bone or other tissues. Tissue materials include, but are not limited to, autograft, allograft, or xenograft, and may be resorbable or non-resorbable in nature. Examples of other tissue materials include hard tissues, connective tissues, demineralized bone matrix, and combinations thereof.

All or a part of the tie 10 may include a polymeric body configured to elute the therapeutic substance. The polymeric body may further elute the therapeutic substance at a predetermined rate. Alternatively or in addition, the tie 10 may at least in part be porous, and the therapeutic substance may be at least in part disposed in the pores of the tie 10.

The tie 10 in whole or in part may comprise a polymeric material into or onto which a therapeutic substance is incorporated. Any polymeric material may be used. The polymeric material may be biocompatible and capable of presenting or eluting the therapeutic substance in an effective amount. Biocompatible polymers may be obtained from natural or synthetic sources, and may be bioresorbable. Examples of natural materials of which the polymer may be composed include collagen, elastin, silk, and demineralized bone matrix. Other examples of suitable polymeric materials include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; polytetrafluoroethylene (PTFE); polyethylene, low density polyethylene; polymethylmethacrylate (PMMA); polyetheretherketone (PEEK); and polyetherketoneketone (PEKK). The polymer may also be a polymeric hydroxyethylmethacrylate (PHEMA). Suitable bioresorbable synthetic polymers include poly(L-lactide), poly(D,L-lactide), poly(L-co-D,L-lactide), polyglycolide, poly(lactide-co-glycolide), poly(hydroxylbutyrate), poly(hydroxyvalerate), tyrosine-derived polycarbonate, polyanhydride, polyorthoester, polyphosphazene, poly(dioxanone), and polyglyconate. Other similar polymers known to the art may be used and various mixtures of polymers may be combined to adjust the properties of the composition as desired.

A therapeutic substance may be incorporated into or coated on a polymeric material of the tie 10 using any known or developed technique. For example, the therapeutic substance may be adhered to a surface of any part of the tie 10, adsorbed into the tie 10, or compounded into the polymeric material that forms the tie 10. Accordingly, the therapeutic substance may be embedded, coated, mixed or dispersed on or in the material of the tie 10. A coating method may be determined by the material of the tie 10 and the therapeutic substance utilized. Such methods include but are not limited to, dipping, spraying, rolling, plating and embedding the coating into the surface by any means. For example, a polymeric tie may be coated by dip or spray coating polymeric resin and crosslinker with the therapeutic substance as substituent or dissolved within the polymer. Curing may be achieved chemically, photochemically or thermally. Other common methods include dip or spray coating water insoluble resin containing a therapeutic substance followed by drying or grafting directly onto the substrate chemically or photochemically.

Additional examples of ways to form at least a portion of the tie 10 include blending a therapeutic substance with a polymer and then forming the polymer into the tie 10, or portion of the tie 10. Alternatively, the therapeutic substance may be in a solution with the polymer to form a coating. The therapeutic substance may be attached to a polymeric material by a chemical modification of the surface such as surface grafting by hydrolyzable linkage of the therapeutic substance to the surface or by photolinking the therapeutic substance to the surface. Surface polymerization, derivatization or absorption may also be used. Other examples of obtaining a surface bound therapeutic substance include any existing means, such as ion implantation, chemical modification of the surface, photochemical or chemical grafting or formation of a crosslinked surface immobilized network. Silver ions, where used, may be deposited on the surface of the tie 10 by vacuum deposition, ion sputtering or surface deposition, among others. The surface of the tie 10 may be pretreated according to known methods such as plasma treatment prior to exposure to the coating material. Where solvents are present in the therapeutic substance, such solvents may be biocompatible if residue remains after the therapeutic substance is applied.

Metals which can be used to form all or a part of the tie 10 include but are not limited to stainless steel and other steel alloys, cobalt chrome alloys, tantalum, titanium, titanium alloys, titanium-nickel alloys such as Nitinol and other superelastic or shape-memory metal alloys. Metals can be formed into supportive frameworks by a variety of manufacturing procedures including combustion synthesis, plating onto a "foam" substrate, chemical vapor deposition (see U.S. Pat. No. 5,282,861), lost mold techniques (see U.S. Pat. No. 3,616,841), foaming molten metal (see U.S. Pat. Nos. 5,281,251, 3,816,952 and 3,790,365), and replication of reticulated polymeric foams with a slurry of metal powder. Sintering of metals and polymers of various types and other methods of forming porous structures to make all or part of the tie 10 may be accomplished as disclosed at least in U.S. Pat. Nos. 6,572,619, and 6,673,075. Metal particles may have to be fused at elevated temperatures and therefore cannot be readily formed directly on surfaces which would be adversely affected by the fusion temperature needed for metal particles. Metal particles may be bonded onto a surface with an adhesive acting to bond the particles with a particle-surface coating matrix which does not fill the pores. By proper selection of the amount (the relative amount of polymer binder to metal), the pore size can be tightly controlled and the metal/binder materials applied to a wide array of surfaces. Various types of polymer binders such as thermoplastic binders (applied by melting the polymer of applied from solution, dispersion, emulsion or suspension or even direct polymerization on the surface of the polymers by heat, catalysis, or radiation), thermoset binders (also provided by reaction on the surface of the particles) or by fusion of the particles (with or without additional cross linking), or the like, may be used. Among the useful classes of polymers would be at least polyamides, polyacrylates, polyurethanes, silicon polymers (e.g., polysiloxanes, silicone rubbers, siloxane graft or block polymers or copolymers, etc.), polyester resins, highly fluorinated resins (e.g., polytetrafluoroethylene), polyimides, and the like. These same classes of polymers may also comprise the mass of the therapeutic substance delivery element itself. Particularly when latices are used to mold the tie 10 or particles are fused (thermally or by solvents) to form the tie 10, the degree of pressure applied, the level of heat applied, the duration of the solvent, and other obvious parameters may be used to control the degree of fusion of the polymer and its degree of porosity. Porosity can also be created in polymeric materials useful for the tie 10 by including a soluble or leachable or flowable pore-leaving component with the polymer, forming the tie, and then removing the pore-leaving component. Techniques in this category include mixing a highly soluble particle (soluble in a solvent in which the polymer is not soluble), such as NaCl, into the polymer. Casting or molding the tie 10, and then leaching out or dissolving out the salt with water. By controlling the volume of salt, and the size of the salt particles, the pore size can be readily controlled. Alternatively, it is known to mix a non-solvent liquid from the polymer to form an emulsion or dispersion. When the polymer is solidified as the tie 10 or component of the tie 10, the non-solvent remains as a dispersed phase which can be readily removed from the tie by washing. Thermoplastic particles may be fused under controlled pressure to form the tie 10 with controlled pore size, as with the ceramics and the metal particles.

Ceramic materials that can be used to form all or a part of the tie 10 include but are not limited to inorganic metal oxides such as aluminum oxide, silica, zirconium oxide, titanium oxide, and composites of mixtures of inorganic oxides. Ceramic materials can be fabricated at both room temperatures and elevated temperatures and so can be provided as both separate materials as part of a tie, and as materials on substrates which could suffer from exposure to elevated temperatures. For example, many ceramics can be formed by solidification (dehydration) of sol-gel dispersions or suspensions of inorganic oxide particles. Other ceramics must be dehydrated and bonded together at elevated temperatures. By controlling the pressure applied to the ceramic material during hardening or fusing, the pore size can be controlled. The use of ceramic-forming particles of different average sizes will also affect the average pore size according to conventional packing and distribution laws. The structure of the tie 10 may be altered to control the elution rate or release rate of the drug. For example, the size of the pores on the outer surface which are exposed to the body liquids is a significant rate limiting factor in the design, while at the same time, the pore size controls the amount of therapeutic substance that can be retained within the tie 10. As the pore size increases internally, larger amounts of therapeutic substance may be stored, while larger pore sizes on the surface increase the therapeutic substance release rate. One design would therefore have pore openings on the surface of the tie 10 with smaller average diameters of the pores than larger pores within the body of the tie 10 which are fluid transferring connected to the pores on the surface of the tie 10. In some embodiments, the interior pores have average pore dimensions which are at least 10-50% greater in average diameter than the pores open at the surface of the tie 10. Combinations of the materials noted above for use in making the tie 10 or portions of the tie 10 may be used in any effective amount or assembly.

The therapeutic substance may comprise one or more of the following: antibiotics, antiseptics, analgesics, bone growth promoting substances, anti-inflammatants, anti-arrhythmics, anti-coagulants, antifungal agents, steroids, enzymes, immunosuppressants, antithrombogenic compositions, vaccines, hormones, growth inhibitors, growth stimulators, and the like. The therapeutic substance may be any drug or bioactive agent which can serve a useful therapeutic or even diagnostic function when released into a patient. More than one therapeutic substance may be present in or on the tie for a particular treatment within the scope of the invention.

Any antibiotic suitable for use in a human may be used in accordance with various embodiments of the invention. As used herein, "antibiotic" means an antibacterial agent. The antibacterial agent may have bateriostatic and/or bacteriocidal activities. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other antibiotics may also be used.

It may be desirable that the one or more antibiotics selected kill or inhibit the growth of one or more bacteria that are associated with infection following surgical implantation of a medical device. Such bacteria may include *Stapholcoccus aureus* and *Staphlococcus epidermis*. The one or more antibiotics selected may be effective against strains of bacteria that are resistant to one or more antibiotics. To enhance the likelihood that bacteria will be killed or inhibited, it may be desirable to combine one or more antibiotics. It may also be desirable to combine one or more antibiotics with one or more antiseptics. Agents having different mechanisms of action and/or different spectrums of action may be most effective in achieving such an effect. In a particular embodiment, a combination of rifampin and minocycline is used.

Any antiseptic suitable for use in a human may be used as or as part of the therapeutic substance. As used herein, "antiseptic" means an agent capable of killing or inhibiting the growth of one or more of bacteria, fungi, or viruses. Antiseptic includes disinfectants. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver sulfadiazine and alcohols. It may be desirable that the one or more antiseptics selected kill or inhibit the growth of one or more microbes that are associated with infection following surgical implantation of a medical device. Such bacteria may include *Stapholcoccus aureus, Staphlococcus epidermis, Pseudomonus auruginosa*, and *Candidia*. To enhance the likelihood that microbes will be killed or inhibited, it may be desirable to combine one or more antiseptics. It may also be desirable to combine one or more antiseptics with one or more antibiotics. Antimicrobial agents having different mechanisms of action and/or different spectrums of action may be most effective in achieving such an effect. In a particular embodiment, a combination of chlorohexidine and silver sulfadiazine is used.

A therapeutic substance, such as an antibiotic or antiseptic, may be present in the tie 10 at any concentration effective, either alone or in combination with another therapeutic substance, to prevent or treat an infection. Generally, a therapeutic substance may be present in the tie 10 at a range of between about 0.5% and about 20% by weight. For example, the therapeutic substance may be present in the tie 10 at a range of between about 0.5% and about 15% by weight or between about 0.5% and about 10% by weight.

The therapeutic substance may comprise an antimicrobial material including metals known to have antimicrobial properties such as silver, gold, platinum, palladium, iridium, tin, copper, antimony, bismuth, selenium and zinc. Compounds of these metals, alloys containing one or more of these metals, or salts of these metals may be coated onto the surface of the tie 10 or added to the material from which the tie 10 is made during the manufacture of the tie 10 or compounded into the base material. One therapeutic substance will contain silver ions and may be obtained through the use of silver salts, such as silver acetate, silver benzoate, silver carbonate, silver iodate, silver iodide, silver lactate, silver laurate, silver nitrate, silver oxide, silver palmitate, silver protein, or silver sulfadiazine, among others. In an embodiment where selenium is used, the selenium may be bonded to the surface of the tie 10, providing an antimicrobial coating.

Therapeutic substances may be chosen based upon a particular application anticipated for a tie. For example, it may be desirable to use a timed release or leachable content material for a particular use. The material comprising the tie may also affect the choice of therapeutic substance. For example, metal ties which are to be provided with therapeutic substance coatings may require therapeutic substances which can be coated onto the metal with satisfactory adhesion to resist the harboring of infectious organisms, or the ability to kill such organisms present throughout the use of the tie. Alternatively, where the therapeutic substance is to be compounded into a metal tie prior to its formation into a tie, the therapeutic substance should be selected so that the therapeutic substance can be readily incorporated into the metal of the tie. In some embodiments, the tie 10 may be at least in part titanium and the therapeutic substance will be silver ion.

Likewise, where the tie 10 comprises a polymeric material, the therapeutic substance may be selected such that the therapeutic substance can be used as a coating material. For example, materials such as silver ions, selenium, and silver zeolite may be used. Separately or in addition, any commercially available additives, such as Heathshield®, among others, may be used.

Use of the tie 10 may provide a positive therapeutic effect by a variety of mechanisms, including preventing adherence of an organism to a surface of the tie 10 or adjacent implant or anatomical structures, providing slow release of a therapeutic substance into the surrounding area, or fixing a source for the therapeutic substance on implant structures for long term effects. The rate of release from a tie, such as the tie 10, may be intended to be highly tailored to the specific use of an associated medical device.

The therapeutic substance may also comprise an osteoconductive, osteogenic, or osteoinductive material. For example and without limitation, the therapeutic substance may include various bioceramic materials, calcium phosphate and other members of the calcium phosphate family, fluorapatite, bioactive glass, and collagen-based materials. Members of the calcium phosphate family include materials such as hydroxyapatite, α-tricalcium phosphate, β-tricalcium phosphate, tetracalcium phosphate, dicalcium phosphate dihydrate, ocatacalcium phosphate, and the like. The therapeutic substance may include an osteoinductive or osteogenic materials such as osteoblast cells, platelet-derived growth factors (PDGFs), bone morphogenetic proteins (BMPs), insulin-like growth factors (IGFs), basic fibroblast growth factor (bFGF), cartilage derived morphogenetic protein (CDMP), growth and differentiation factors (GDFs), LIM mineralization proteins, transforming growth factor beta family (TGF-β), and other bone proteins, such as CD-RAP. These proteins can be recombinantly produced or obtained and purified from an animal that makes the proteins without the use of recombinant DNA technology. Recombinant human BMP is referred to as "rhBMP"; recombinant human GDF is referred to as "rhGDF". Any bone morphogenetic protein is contemplated, including bone morphogenetic proteins designated as BMP-1 through BMP-18. Mimetics of growth factors can also be used in the devices of the present invention for inducing the growth of bone.

Each BMP may be homodimeric, or may be heterodimeric with other BMPs (e.g., a heterodimer composed of one monomer each of BMP-2 and BMP-6) or with other members of the TGF-β superfamily, such as activins, inhibins and TGF-β 1 (e.g., a heterodimer composed of one monomer each of a BMP and a related member of the TGF-β superfamily). Any of these substances may be used individually or in mixtures of two or more. One or more statins may also be included in the therapeutic substance. Non-limiting examples of statins that may be included in the devices of the present invention include atorvastatin, cerivastatin, fluvastatin, lovastatin, mavastatin, pitavastatin, pravastatin, rosuvastatin and simvastatin. The therapeutic substance may include various other organic species known to induce bone formation, and combinations thereof.

The therapeutic substance may also or in addition include pharmaceuticals that target particular cells, such as but not limited to, cancer cells.

Three medical implants 1A, 1B, 1C are shown in FIG. 3 in combination with a spinal rod and screw system in various configurations. The spinal rod and screw system includes three pedicle screws 31, 32, 33 and a spinal rod 39. The medical implant 1A is shown in combination with the spinal rod 39. In the illustrated embodiment, a strap 11 extends around the spinal rod 39 to capture the spinal rod 39 within the loop 15 (FIG. 2) formed by the strap 11 of the tie 10 of the medical implant 1A.

The medical implant 1B also is shown in combination with the spinal rod 39. The medical implant 1B includes a strap 11 that extends around the spinal rod 39 to capture the spinal rod 39 within the loop 15 (FIG. 2) formed by the tie 10 of the medical implant 1B. The medical implant 1B is additionally shown simultaneously in combination with a pedicle screw 32 and the spinal rod 39. The pedicle screw 32 includes a shaft 34 and a receiver 35. As illustrated in FIG. 3, the spinal rod 39 is coupled with the receiver 35 of the pedicle screw 32. The strap 11 of the medical implant 1B is shown extending around the spinal rod 39 at a first side of the spinal rod 39. As illustrated, the first side of the spinal rod 39 is the bottom of the spinal rod 39. The strap 11 is also shown adjacent to the receiver 35 on the near side, as illustrated, of the receiver 35 where the strap 11 extends around the bottom of the spinal rod. The medical implant 1B shown further extends around the spinal rod 39 at a second side of the spinal rod 39 (top side of the spinal rod 39 as illustrated) that is adjacent to a second substantially opposite side of the receiver 35 such that the medical implant 1B captures the spinal rod 39 and the receiver 35 within the loop 15 (FIG. 2) formed by the strap 11 of the tie 10 of the medical implant 1B.

The medical implant 1C also is shown in combination with a bone screw embodied in the pedicle screw 33. The pedicle screw 33 is an example of a bone screw that includes at least a shank 36 and an enlarged head. The enlarged head is embodied in a receiver 37. In other embodiments, the enlarged head may be a screw head that is formed as part of the bone screw, a washer, or any other device of generally larger diameter or size than an associated screw shank. The strap 11 of the medical implant 1C extends around the shank 36 to capture the shank 36 within the loop 15 (FIG. 2) formed by the strap 11 of the tie 10 of the medical implant 1C.

Figure 4:
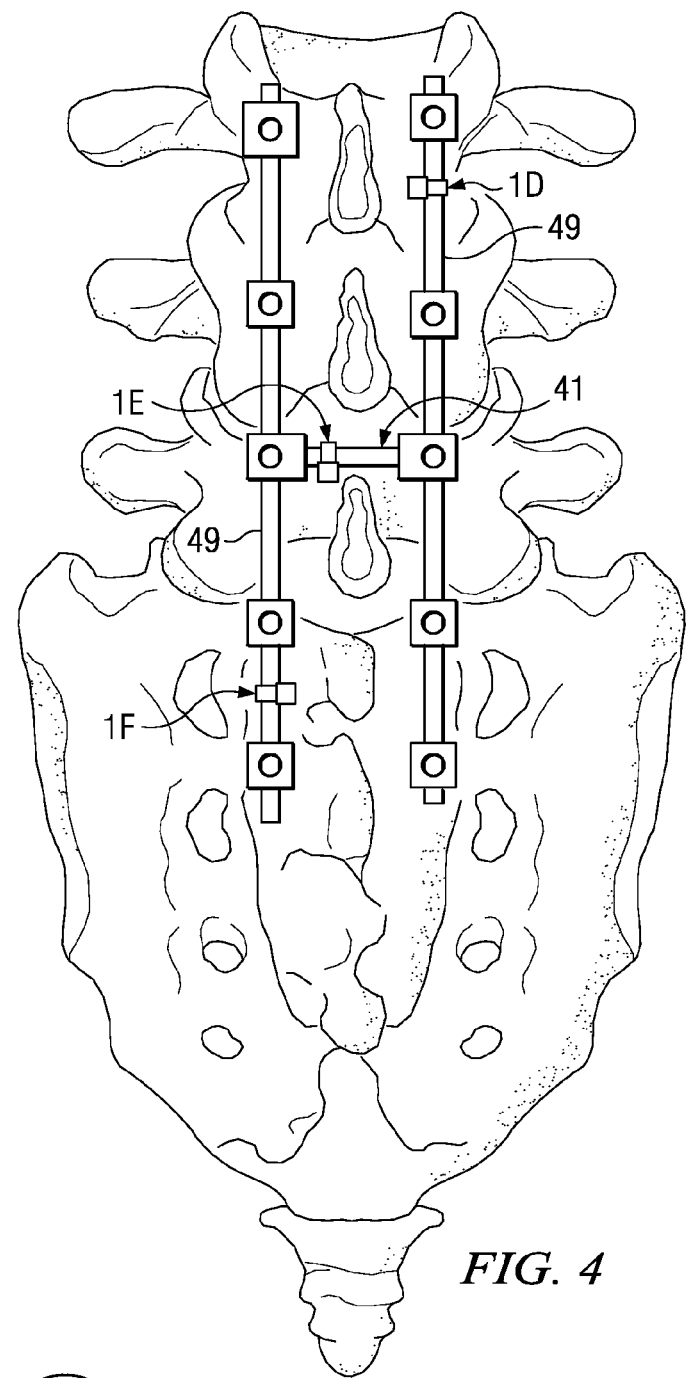
FIG. 4 is an elevation view of embodiments of a medical implant coupled to a spinal rod, screw, and cross-link construct in place on portions of a sacral and lumbar spine.
Figure 5:
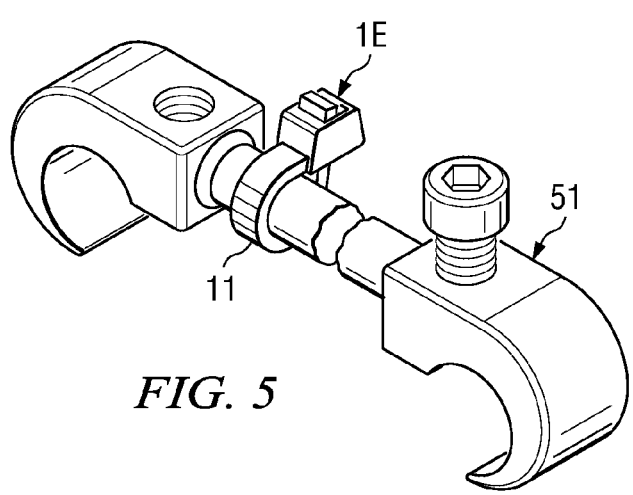
FIG. 5 is a perspective view of an embodiment of a medical device coupled to a spinal cross-link.

FIG. 4 illustrates three medical implants 1D, 1E, 1F coupled to a spinal rod, screw, and cross-link construct. The spinal rod, screw, and cross-link construct is in place on portions of a sacral and lumbar spinal segment. The medical implants 1D and 1F are shown in combination with respective spinal rods 49. Configurations and embodiments of the medical implants 1D and 1F are substantially similar to the embodiments described in association with the medical implant 1A herein. The medical implant 1E is shown in combination with a cross-link 41. The cross-link 41 is configured to extend between the spinal rods 49. The medical implant 1E includes a strap 11 that extends around the cross-link 41 to capture the cross-link 41 within the loop 15 (FIG. 2) formed by the strap 11 of the tie 10 of the medical implant 1E. An alternate embodiment of a cross-link 51 is illustrated in FIG. 5. The medical implant 1E similarly is shown in FIG. 5 extending around the cross-link 51 to capture the cross-link 51 within the loop 15 (FIG. 2) formed by the strap 11 of the tie 10 of the medical implant 1E. The cross-link 51 is shown with a broken section to illustrate that it may be of any functional length.

Figure 6:
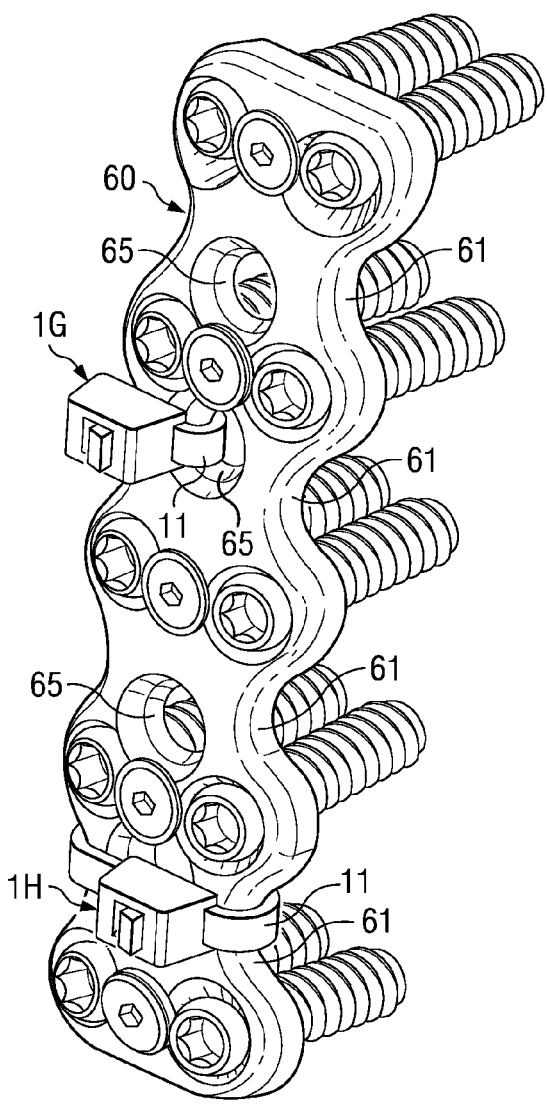
FIG. 6 is a perspective view of embodiments of a medical implant coupled to a spinal plate in various configurations.

Two medical implants 1H, 1G are shown in FIG. 6 in combination with a bone plate 60 and associated hardware. More particularly, the illustrated bone plate 60 is a four level spinal plate. In other embodiments, the bone plate may be a general orthopedic plate or a spinal plate of any size or configuration. For example and without limitation, a spinal plate may be configured to stabilize or fuse one or more levels, or may be configured for placement from any surgical approach or for any surgical placement, such as anterior, posterior, lateral, and variations oblique by some degree from each. Configurations and embodiments of the medical implants 1G and 1H are substantially similar to the embodiments described in association with the medical implant 1A herein. The medical implant 1G is shown in combination with the bone plate 60 around which a strap 11 of the medical implant 1G extends to capture portions of the bone plate 60 within the loop 15 (FIG. 2) formed by the strap 11 of the tie 10 of the medical implant 1G. The bone plate 60 includes multiple openings 65. The illustrated openings 65 are round and are intended to provide sight holes for alignment of the bone plate 60 with the anatomy of a patient, but in other embodiments the openings 65 may be of any configuration and for any purpose. In the illustrated embodiment, the strap 11 of the medical implant 1G extends through the opening 65 to capture a portion of the bone plate 60 within the loop 15 (FIG. 2).

The medical implant 1H is shown in combination with the bone plate 60 around which a strap 11 of the medical implant 1H extends to capture portions of the bone plate 60 within the loop 15 (FIG. 2) formed by the strap 11 of the tie 10 of the medical implant 1H. The bone plate 60 includes multiple portions with a relatively smaller cross-sectional area 61. At least a portion of each of the straps 11 of the medical implants 1G and 1H extends around respective relatively smaller cross-sectional areas 61 of the bone plate 60. Each of the medical implants 1G and 1H of the illustrated embodiment is also configured to be adjacent to a spinal disc of a patient when the bone plate 60 is implanted as an anterior fusion plate.

Figure 7:
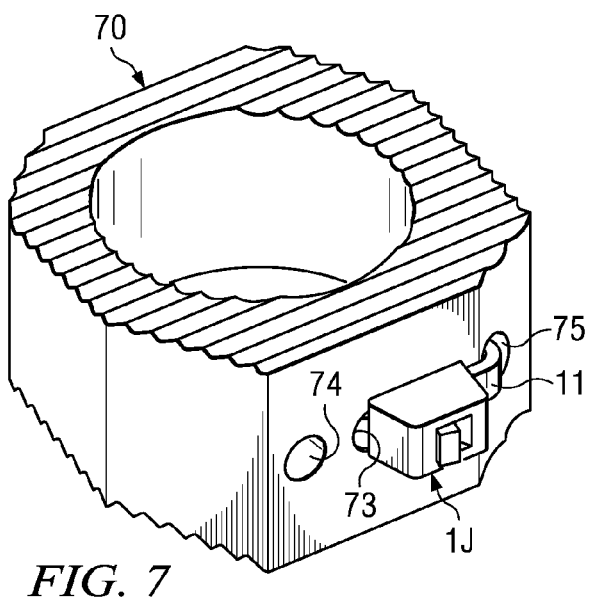
FIG. 7 is a perspective view of an embodiment of a medical implant coupled to an interbody implant.

A medical implant 1J is shown in combination with an interbody implant 70 in FIG. 7. Configurations and embodiments of the medical implant 1J are substantially similar to the embodiments described in association with the medical implant 1A herein. The illustrated interbody implant 70 is configured to space apart lumbar vertebrae and is configured for insertion from anterior and oblique approaches. However, in other embodiments, an interbody implant may be of any size or shape and configured for use in any spinal region and for insertion from any approach. The interbody implant 70 in particular includes two threaded inserter holes 73, 75 and an alignment hole 74. The medical implant 1J includes a strap 11 that extends to capture a part of the interbody implant 70 with the loop 15 (FIG. 2) formed by the strap 11 of the tie 10 of the medical implant 1J. In particular with the embodiment shown, the strap 11 extends through the inserter holes 73, 75 to capture a portion of the interbody implant that is between the inserter holes 73, 75 within the loop 15. In other embodiments, other portions and devices of an interbody implant may be used to capture the interbody implant, such as but not limited to, the alignment hole 74.

Figure 8:
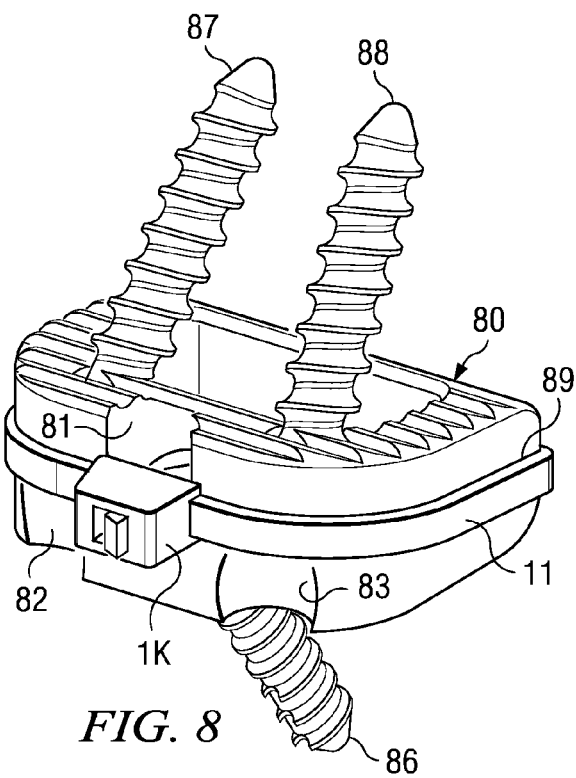
FIG. 8 is a perspective view of an embodiment of a medical implant coupled to an interbody implant.

A medical implant 1K is shown in combination with an interbody implant 80 in FIG. 8. Configurations and embodiments of the medical implant 1K are substantially similar to the embodiments described in association with the medical implant 1A herein. The illustrated interbody implant 80 is configured to space apart lumbar vertebrae and is configured for insertion from an anterior approach. However, in other embodiments, an interbody implant may be of any size or shape and configured for use in any spinal region and for insertion from any approach. The interbody implant 80 includes three holes 81, 82, 83 for receiving respective anchoring screws 86, 87, 88. The medical implant 1K includes a strap 11 that extends to capture the interbody implant 80 with the loop 15 (FIG. 2) formed by the strap 11 of the tie 10 of the medical implant 1K. In particular with the embodiment shown, the strap 11 extends around the entire interbody implant 80 to capture the interbody implant 80. In some embodiments, the strap 11 of the medical implant 1K may be aligned and retained within a slot 89 to maintain the medical implant 1K in a particular orientation relative to the interbody implant 80. The strap 11 of the medical implant 1K of the illustrated embodiment extends around the interbody implant 80 and in part blocks the three holes 81, 82, 83. The medical implant 1K may by this mechanism also assist in preventing the anchoring screws 86, 87, 88 from backing out of bone in which they are implanted. In other embodiments, a strap of a medical implant may be used to block a hole through which graft material is inserted into an interbody implant or to retain graft material within an interbody implant, or for any other useful purpose.

Figure 9:
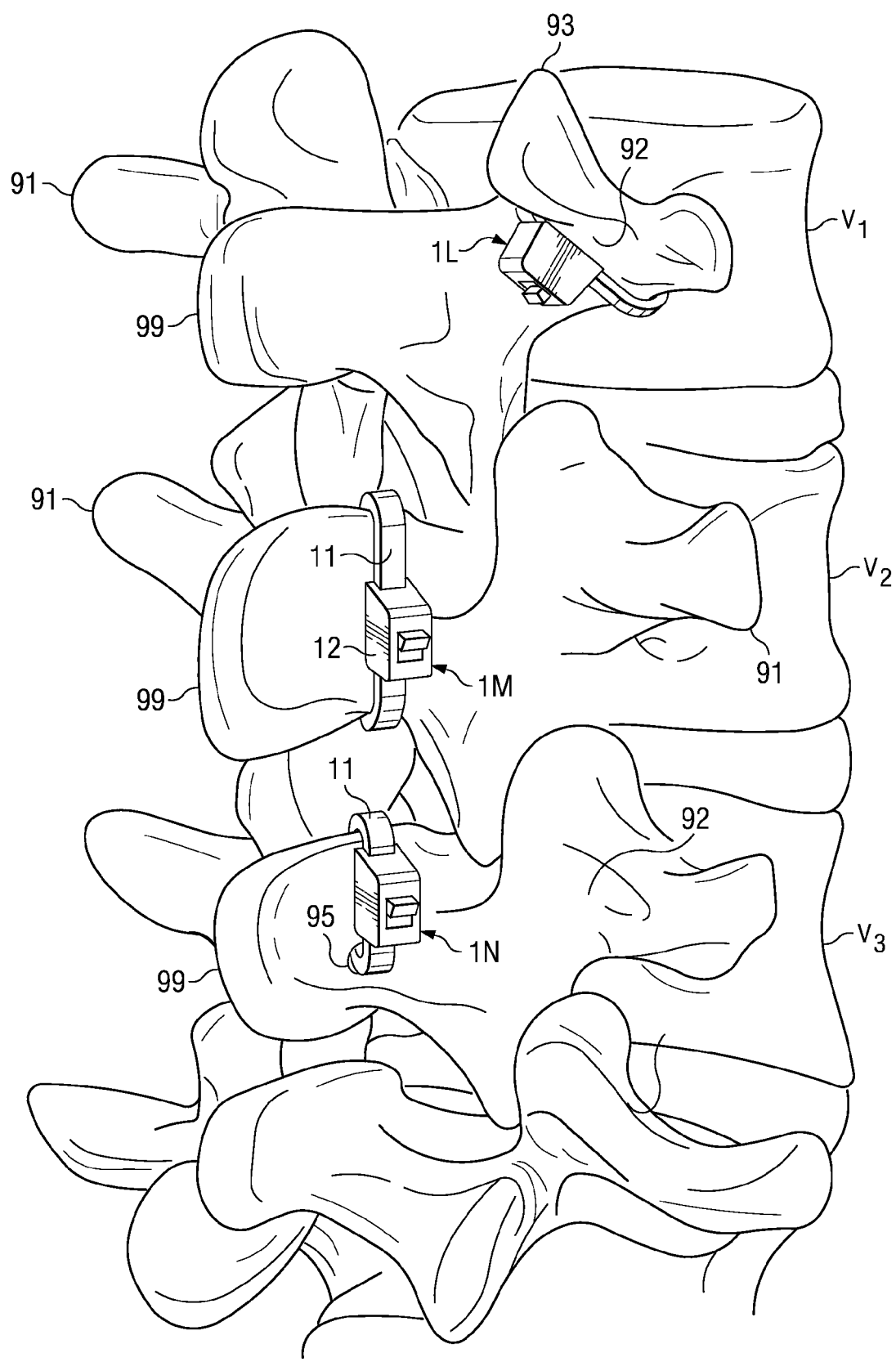
FIG. 9 is a perspective view of embodiments of a medical implant coupled to various spinal structures.

Medical implants 1L, 1M, and 1N are shown in FIG. 9 coupled to various spinal structures of lumbar vertebrae $V_1$ and $V_2$. The implants 1L, 1M, and 1N are shown coupled to bony spinal structures, but may also be coupled to other anatomical structures in various embodiments. The medical implant 1L is shown coupled around portions of a pedicle region 92 and a superior articular process 93. Medical implants 1M and 1N are shown coupled around portions of respective spinous processes 99. Other medical implants may be coupled around anatomical structures, such as but not limited to, any portion of a transverse process 91, another portion of the spinous process 99, the pedicle region 92, the superior articular process 93, a lamina, or any of these or other regions that are altered to create on or more coupling points.

The tie 10, and all tie embodiments, may be either placed during the implantation of existing implant systems or may be placed after components of existing implant systems have already been implanted. Therefore, the sequences for placing each of the listed ties are complementary to existing surgical procedures.

The distal ends 19 of the straps 11 of the medical implants 1A, 1B, 1C are shown implanted with the respective medical implants. In contrast, distal ends of the medical implants 1D, 1E, 1F, 1G, 1H, 1J, 1K, 1L, 1M, and 1N have been removed. The distal ends 19 of some embodiments may be left in place and implanted with a medical implant 1. However, the distal end 19 of any strap 11 may be removed to avoid interaction with anatomical structures, as is deemed appropriate by a surgeon. A distal end of a strap may be removed by cutting with a tool. In addition or alternatively, a strap may include areas of reduced cross-sectional area and/or reduced strength where a distal end of the strap may be removed with the assistance of a tool and/or by bending, twisting, or by any effective action.

A method of applying the therapeutic substance may include making an incision in a patient, inserting a medical device, receiving a tie that incorporates a therapeutic substance, wrapping a strap of the tie around at least a portion of a medical device, and tightening a loop of the tie to connect the tie to the medical device. A non-limiting example tie is the tie 10 describe in more detail in FIGS. 1 and 2. The tie 10 includes the strap 11 and the pawl 12. The pawl 12 is configured to receive the strap 11 to form the loop 15 that includes portions of strap 11 and the pawl 12. In the illustrated embodiment, the strap 11 includes the distal end 19 that is free to wrap around at least a portion of a medical device. In other embodiments, a strap may wrap around a medical device or anatomical structure without having a free end. A captured medical device may be any medical device, and in some embodiments will be one or more of the medical devices illustrated in FIGS. 3-8. The act of tightening the loop 15 of the illustrated embodiment includes moving the strap 11 relative to the pawl 12. The strap 11 may be moved by pulling on the strap 11 directly or by use of a general purpose grasping instrument or specialized instrument. One specialized instrument embodiment would contact the pawl 12, move the strap 11 relative to the pawl 12, and also be configured to optionally cut off the strap 11 at or near the pawl 12. Other embodiments may include the act of detaching at least a portion of a distal end of a strap by any effective action or device.

Another method embodiment includes applying a similar tie to an anatomical structure. The anatomical structure may be a spinal structure such as the spinal bony structures described in more detail in association with FIG. 9 or any other anatomical structure where application of a therapeutic substance may be beneficial. As a non-limiting example, a method in association with the medical implant 1M of FIG. 9 is described. The example method may include making an incision in a patient. The example method may include applying a therapeutic substance to a patient by receiving the tie 10 of the medical implant 1M, where the tie 10 includes an incorporated therapeutic substance. The tie 10 may include therapeutic substance in one or both of the strap 11 and the pawl 12, as describe in detail above. An act of the example method includes wrapping the strap 11 around at least a portion of an anatomical structure, such as the illustrated spinous process 99. Another act of the example embodiment includes tightening the loop 15 (FIG. 2), comprising the strap 11 and the pawl 12, by moving the strap 11 relative to the pawl 12 to connect the tie 10 to the patient. In some embodiments, a method may also include making a passage though an anatomical structure and passing at least a portion of the strap 11 through the passage during the act of wrapping the strap 11 around at least a portion of the anatomical structure. For example, as illustrated in FIG. 9, a passage 95 has been made in a spinous process 99. The strap 11 of the medical implant 1N has been passed through the spinous process 99 in the act of wrapping the strap 11 of the medical implant 1N around at least a portion of the spinous process 99. The size, final tightening, and other characteristics of acts of the method may be dictated by the anatomical structure to which a tie is coupled. For example, where a tie is wrapped around a bony structure that includes a periosteum layer with blood vessels and nerves, the tightness or width of the tie may be altered or the tie may include ridges or other devices that allow unpressured areas of tissue to preserve the health of the bony structure. Some embodiments may include the act of detaching at least a portion of a distal end of a strap by any effective action or device, including but not limited to cutting the strap off.

All patents and applications specifically list by number herein are hereby incorporated by reference herein in their entirety.

Various method embodiments of the invention are described herein with reference to particular medical implants. However, in some circumstances, each disclosed method embodiment may be applicable to each of the medical implants, or to some other medical implant operable as disclosed with regard to the various method embodiments.

Terms such as around, near, opposite, below, distal, top, bottom, side and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A medical implant configured to deliver a therapeutic substance after a surgical procedure comprising:
   a tie configured to couple with one or more of a medical device and an anatomical structure after the medical device is implanted, the tie comprising: a strap, and a pawl configured to receive the strap to form a loop comprising at least a portion of the strap and at least a portion of the pawl, the strap including a removable distal end; and
   a time-release therapeutic substance incorporated with the tie; wherein the strap is retained in the pawl and prevented from moving out of the pawl as the strap is advanced into the pawl to lock the size of the loop at a progressively smaller size and at least a portion of the removable distal end of the strap is removed once the distal end is advanced through the pawl; and
   wherein the tie is configured to release at least a portion of the therapeutic substance after the surgical procedure is completed when the tie is exposed to an at least in part aqueous substance; and
   wherein the tie has at least a first set and a second set of pore openings for delivering the therapeutic substance, the first set of pore openings present on a surface of the tie and the second set of pore openings present within a body of the tie, the first set of pores having a smaller average diameter of pores as compared to the average diameter of pores of the second set of pores.

2. The medical implant of claim 1 wherein the tie comprises a polymeric material incorporating the therapeutic substance.

3. The medical implant of claim 2 wherein the polymeric material is configured to elute the therapeutic substance at a predetermined rate.

4. The medical implant of claim 1 wherein the therapeutic substance is at least in part disposed in the first set and the second set of pore openings of the tie.

5. The medical implant of claim 1 wherein the therapeutic substance is incorporated at least in the strap.

6. The medical implant of claim 1 wherein the therapeutic substance is incorporated at least in the pawl.

7. The medical implant of claim 1 wherein the therapeutic substance includes one or more of: antibiotic, antiseptic, analgesic, bone growth promoting substance, anti-inflammatant, anti-arrhythmic, anti-coagulant, antifungal agent, steroid, enzyme, immunosuppressant, antithrombogenic composition, vaccine, hormone, growth inhibitor, and growth stimulator.

8. The medical implant of claim 1 in combination with a spinal rod around which the strap at least in part extends to capture the spinal rod within the loop formed by the tie.

9. The medical implant of claim 1 in combination with a bone screw that comprises a shank and an enlarged head coupled with the shank, and wherein the strap at least in part extends around the shank to capture the shank within the loop formed by the tie.

10. The medical implant of claim 1 in combination with a spinal rod and a pedicle screw wherein the spinal rod is coupled with a receiver of the pedicle screw, and wherein the strap at least in part extends around the spinal rod at a first side of the spinal rod adjacent to the receiver on a first side of the receiver, and extends around the spinal rod at a second side of the spinal rod that is substantially opposite from the first side of the spinal rod and that is adjacent to a second side of the receiver that is substantially opposite from the first side of the receiver such that the medical implant captures the spinal rod and the receiver within the loop formed by the tie.

11. The medical implant of claim 1 in combination with a cross-link configured to extend between spinal rods around which the strap at least in part extends to capture the cross-link within the loop formed by the tie.

12. The medical implant of claim 1 in combination with an interbody implant around which the strap at least in part extends to capture at least a part of the interbody implant within the loop formed by the tie.

13. The medical implant and interbody implant of claim 12 wherein the interbody implant includes a device for engaging with an implant inserter, and the strap extends at least in part through the device for engaging with an implant inserter to capture at least a part of the interbody implant within the loop formed by the tie.

14. The medical implant and interbody implant of claim 12 wherein the interbody implant includes at least one hole, and the strap extends at least in part around the interbody implant to at least in part block the at least one hole.

15. A medical implant configured to deliver a therapeutic substance after a surgical procedure comprising:
   a tie configured to couple with one or more of a medical device and an anatomical structure after the medical device is implanted, the tie comprising: a strap, and a pawl configured to receive the strap to form a loop comprising at least a portion of the strap and at least a portion of the pawl, the strap including a removable distal end; and
   a therapeutic substance incorporated with the tie; wherein the strap is retained in the pawl and prevented from moving out of the pawl as the strap is advanced into the pawl to lock the size of the loop at a progressively smaller size as the strap is advanced into the pawl and at least a portion of the removable distal end of the strap is removed once the distal end is advanced through the pawl; and a four level spinal plate around which the strap at least in part extends to capture at least a part of the spinal plate within the loop formed by the tie, wherein the strap extends around a portion of the spinal plate with a relatively smaller cross-sectional area such that at least a portion of the strap is configured to be substantially adjacent to a spinal disc when the spinal plate is implanted, wherein the tie is configured to release at least a portion of the therapeutic substance at a predetermined rate after the surgical procedure is completed when the tie is exposed to an at least in part aqueous substance, and wherein the tie comprises a polymeric material incorporating the therapeutic substance, the polymeric material configured to elute the therapeutic substance at a predetermined rate, the therapeutic substance present in the tie within a range of between 0.5% to about 20% by weight.

16. The medical implant and bone plate of claim 15 wherein the spinal plate includes an opening through which the strap extends to capture at least a part of the spinal plate within the loop formed by the tie.

17. A method of applying a therapeutic substance comprising:

providing the medical implant of claim 1;

wrapping the strap of the medical implant of claim 1 around at least a portion of a medical device; and tightening the loop of the medical implant of claim 1 by moving the strap relative to the pawl of the medical implant of claim 1 to connect the tie of the medical implant of claim 1 to the medical device.

18. The method of claim 17 wherein the strap includes a distal end that is received through the pawl and extended from the pawl while tightening the loop, the method further comprising detaching at least a portion of the distal end of the strap.

19. The method of claim 17, further comprising making a passage though an anatomical structure and passing at least a portion of the strap through the passage so as to wrap the strap around at least a portion of the anatomical structure.

20. The method of claim 19 wherein the strap includes a distal end that is received through the pawl and extended from the pawl while tightening the loop, the method further comprising detaching at least a portion of the distal end of the strap.

* * * * *